United States Patent [19]
Gottlieb

[11] Patent Number: 5,460,971
[45] Date of Patent: * Oct. 24, 1995

[54] SENSOR APPARATUS AND ANALYTICAL METHOD

[76] Inventor: Amos J. Gottlieb, 1650 Haight St., San Francisco, Calif. 94117

[*] Notice: The portion of the term of this patent subsequent to Sep. 14, 2010 has been disclaimed.

[21] Appl. No.: 74,964

[22] Filed: Jun. 11, 1993

Related U.S. Application Data

[62] Division of Ser. No. 803,735, Dec. 9, 1991, Pat. No. 5,244,810, which is a continuation of Ser. No. 464,531, Jan. 12, 1990, abandoned.

[51] Int. Cl.$^6$ ..................................................... G01N 21/63
[52] U.S. Cl. ........................... 436/68; 436/138; 436/167; 436/172; 436/178; 422/82.06; 422/82.07; 128/634
[58] Field of Search ............................. 422/82.05, 82.06, 422/82.07, 82.08, 82.09, 91, 82; 436/122, 140, 68, 136, 138, 167, 168, 172, 175, 178; 128/634

[56] References Cited

U.S. PATENT DOCUMENTS

| | | | |
|---|---|---|---|
| 4,476,870 | 10/1984 | Peterson et al. | 128/634 |
| 4,892,383 | 1/1990 | Klainer et al. | 436/164 X |
| 5,116,759 | 5/1992 | Klainer et al. | 422/82.05 X |
| 5,242,835 | 9/1993 | Jensen | 436/167 X |

OTHER PUBLICATIONS

Milanovich, et al., Advances in Instrumentation, vol. 38, part 1, pp. 407–418 (1983).

*Primary Examiner*—Jeffrey R. Snay
*Attorney, Agent, or Firm*—Burns, Doane, Swecker & Mathis

[57] ABSTRACT

This invention provides a fiber-optic sensor or analytical apparatus and associated method which utilizes the combination of (a) a solid, semi-solid or liquid sensor body which is capable of selectively dissolving the analyte compound to be detected and analyzed into the sensor body from the mixture or environment in which the compound is present and excluding undesired or interfering components, (b) a radiation source for directly radiating the analyte compound molecules to excite same to an elevated energy state, thereby causing the analyte compound itself to luminesce while dissolved in the sensor body, and (c) a radiation detector for detecting and measuring the light emitted from the excited analyte compound molecules when they return to a lower energy state. The selective dissolving sensor body provides a controlled environment in which both the source light directly excites the analyte molecules and the excited molecules emit light which is detected and measured. This invention thereby provides dual selectivity, first by selectively dissolving the analyte component into the sensor body and second by the direct selective/specific excitation of the analyte compound to cause it to specifically luminesce in a manner known to be characteristic of that compound. Improved sensitivity also is provided by this invention by the direct measurement relationship, i.e, the higher the concentration of the analyte compound, the greater the luminescent signal from the excited analyte compound.

21 Claims, 4 Drawing Sheets

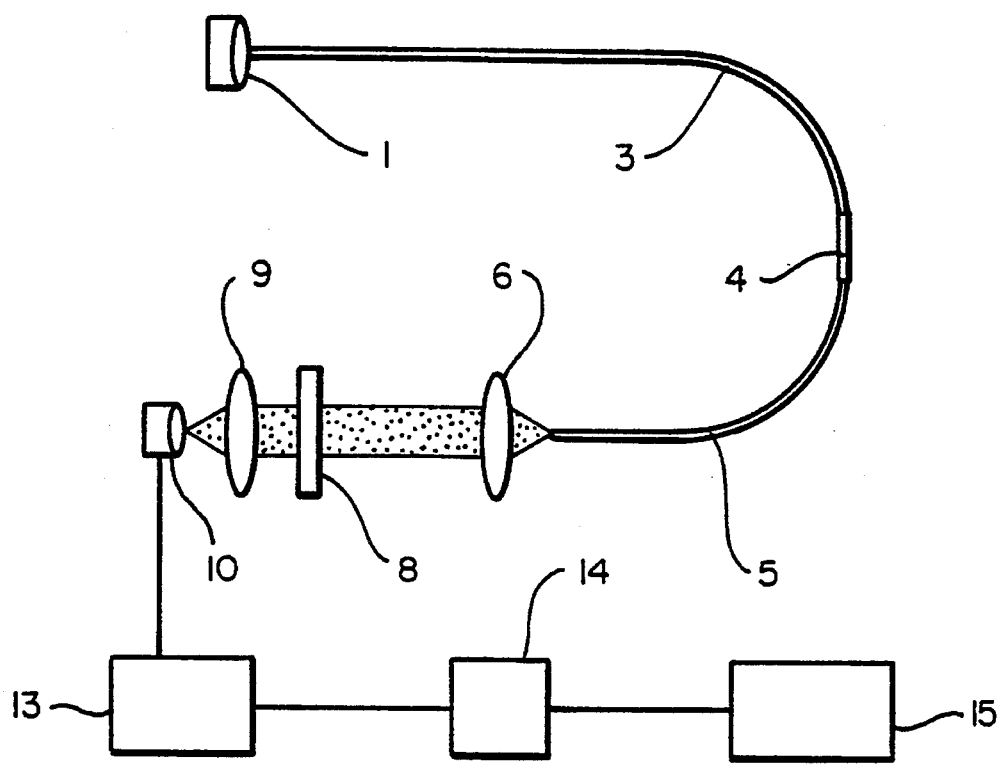
FIG_1
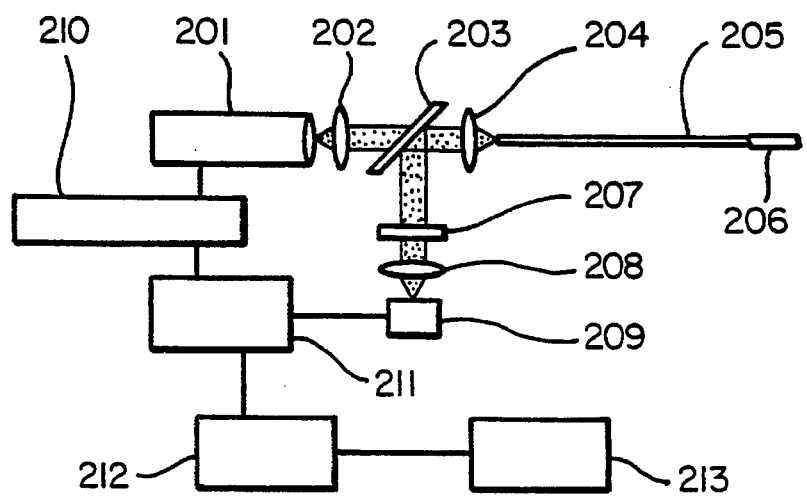
FIG_2

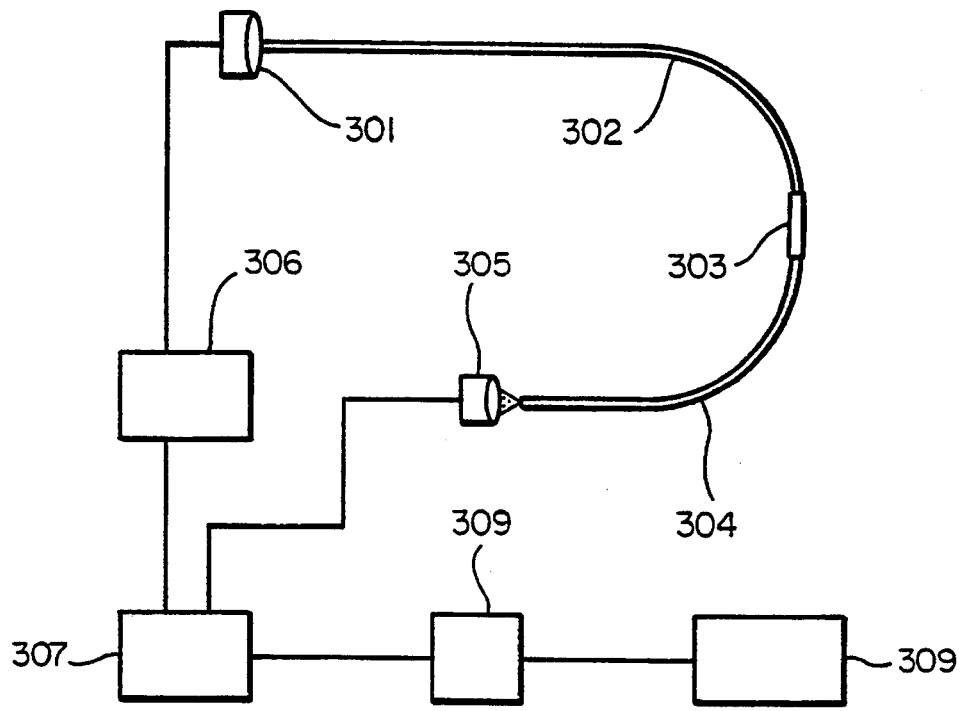
FIG_3
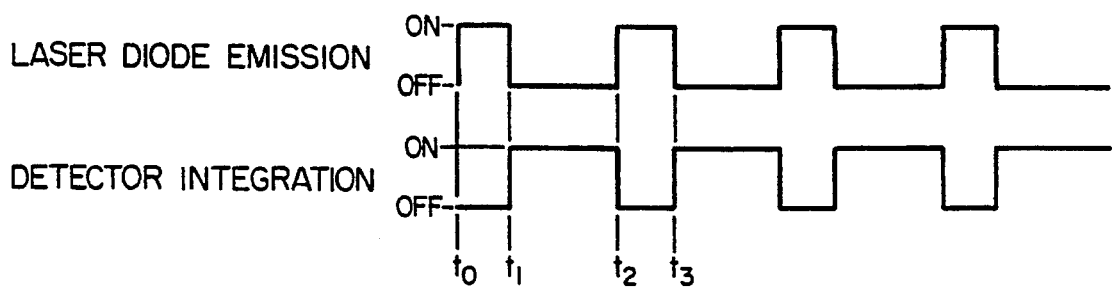
FIG_4

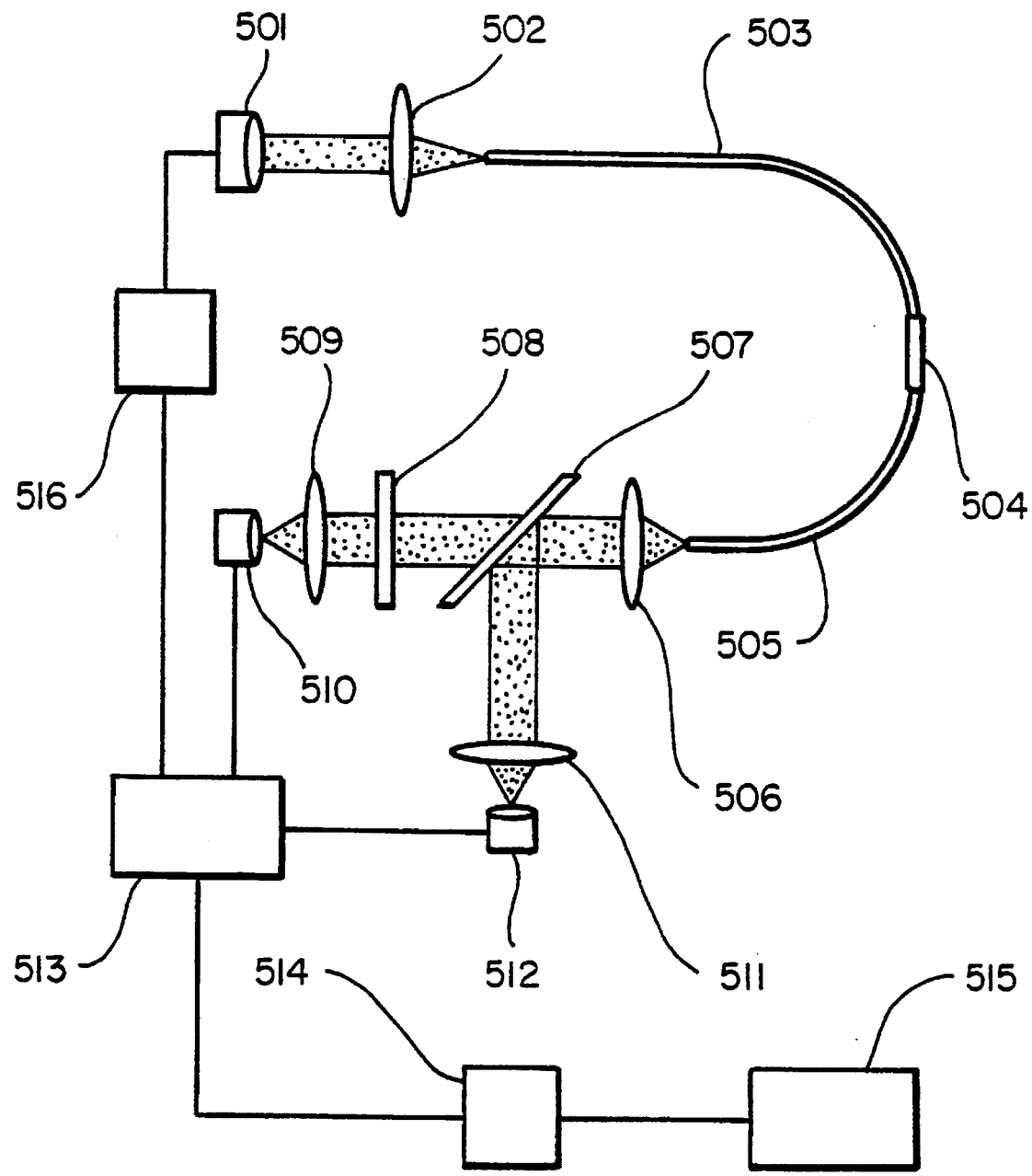
FIG_5

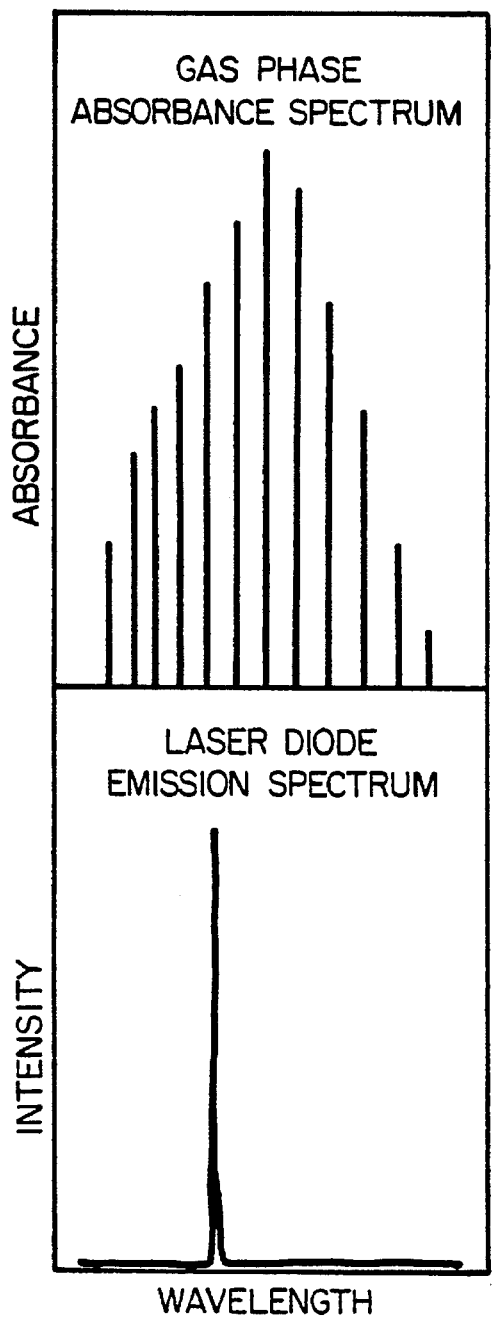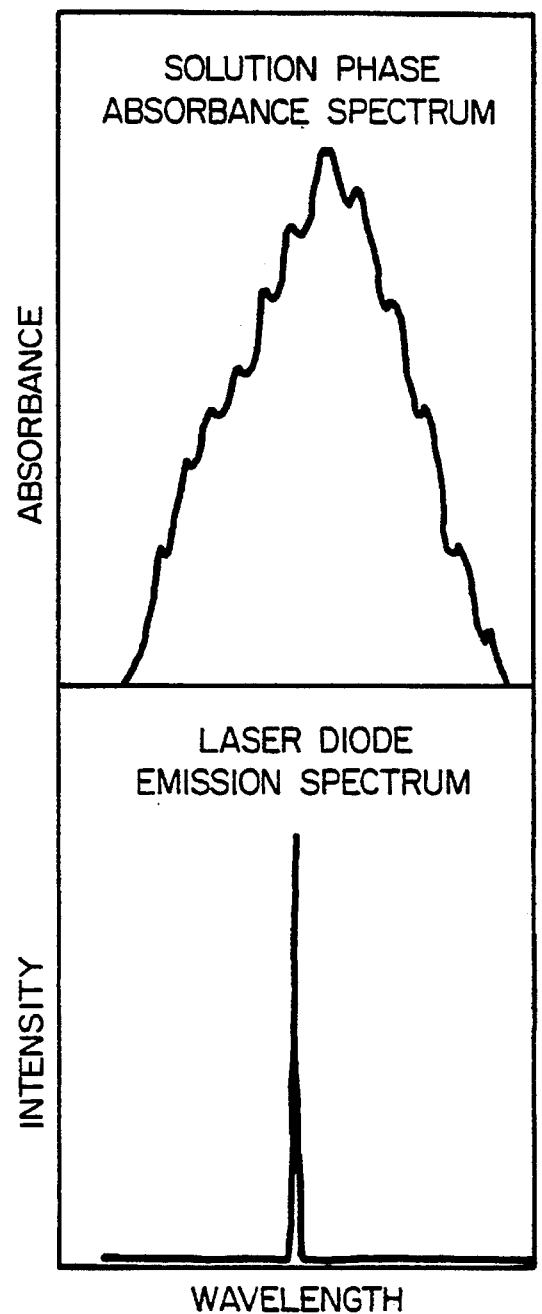
FIG_6a       FIG_6b

SENSOR APPARATUS AND ANALYTICAL METHOD

This application is a divisional of application Ser. No. 07/803,735, filed Dec. 9, 1991, now U.S. Pat. No. 5,244,810, which was a continuation of application Ser. No. 07/464,531, filed Jan. 12, 1990, now abandoned.

FIELD OF THE INVENTION

This invention relates to analytical sensors and methods for measuring the concentration of a particular component in a fluid mixture, such as an aqueous solution, and particularly relates to analytical apparatus and methods for measuring oxygen levels in blood.

BACKGROUND OF THE INVENTION

There are numerous sensor and analytical devices known in the art based on the use of optical signals. These devices are generally of the following three types of devices.

The first type of device employs indicator compositions which interact with the gas or other selected component being detected and measured and/or interact with a source of incident radiant energy. The indicator either fluoresces in response to the presence of the component and/or light signal, or causes some other change which is detected as an indication of the presence and concentration of the selected component. Examples of devices utilizing indicator compositions include those disclosed in U.S. Pat. Nos. Re. 31,879 to Lubbers, 3,612,866 to Stevens, 4,321,057 and 4,399,099 to Buckles, 4,476,870 to Peterson et al., and 4,737,343 to Hirschfeld.

There are a number of problems associated with the use of indicators. The indicator compounds and compositions are basically dyes which have specific characteristics, such as a particular fluorescence under particular conditions or particular interaction with other materials. As with any dye composition, it is extremely difficult to obtain a dye which does not bleach when exposed to the light used or does not change chemically over time. Changes particularly occur when the indicator composition is exposed to a working environment, which may severely and adversely affect the fluorescent or other properties of the indicator. When the indicator composition properties change, its fluorescent indications change, often in an unpredictable way. It is difficult to compensate for such changes in an indicator in order to maintain accurate analytical results, particularly because it is usually not known exactly when or to what extent an indicator undergoes a change. Thus, erroneous analytical results can be obtained from the sensor until the change in the indicator is detected and compensated for or the indicator replaced. Reliability of sensor devices utilizing indicator compositions is difficult to achieve, particularly long term.

Other disadvantages of these devices result from the fact that many of the indicator compositions are difficult to make and the fact that additional problems are encountered in placing the indicators in suitable polymers or adhering them to materials in such a way that they are immobilized and useful on a continuing basis in an analytical device. See 4,657,736 to Marsouer, et al., 4,712,865 to Hsu et al., and 4,849,172 to Yafuso, et al. Another disadvantage, which many of the above devices have, results from sensor systems that make use of the technique of quenching the fluorescence of the indicator. In such a system, the indicator gives its strongest signal or fluorescence in the absence of the component being detected and measured. When that component such as oxygen, is present, the fluorescence of the indicator is quenched or decreased, thus providing an inverse response of the fluorescent light to the presence of the compound being measured. In many applications, a direct response is desired in order to achieve a desired sensitivity.

The second type of device is based on absorbance of light or radiant energy. Examples of absorbance type devices are described in U.S. Pat. Nos. 4,096,388 to Wong, 4,201,222 to Haase, and 4,800,886 to Nester. Generally, the compound in question is received into a chamber or a polymer body where an incident light source is directed into the chamber or polymer body where a compound is present. The absorbance of light in the polymer body or in the chamber varies with the amount of the compound present. The remaining, unabsorbed light is detected and the concentration of the compound is then correlated to the amount of absorbed light. In this type of system, the difficulty is in achieving the desired combination of sensitivity and selectivity. The incident energy can be absorbed or lost due to unknown reasons or is absorbed by other components that are present other than the one of interest, thus giving rise to false positives and inaccurate indications.

The third type of device is based on the fluorescence of the component itself under an incident light source. See U.S. Pat. Nos. 3,795,812 to Okabe and 4,272,486 to Harmon. In these devices, the component is received into a chamber in gas phase, irradiated with a light source to cause the component to fluoresce, and the fluorescent light detected to measure the presence of the component. A difficulty encountered with this type of device is that other undesired materials present in the chamber can also fluoresce in response to the incident light, thus giving false positives and erroneous indications. Harmon discloses a system for pretreating the gas samples to convert or remove such undesired materials before analyzing the sample in the chamber.

In view of the above, disadvantages and deficiencies in the prior art devices, and for other reasons, it is an object of this invention to provide a sensor apparatus and method which eliminates the necessity of using indicator compositions and thereby eliminates the associated problems presented by indicator compositions.

It is another object of this invention to provide a sensor apparatus and method having improved sensitivity and having improved selectivity to eliminate false indications.

It is another object of this invention to provide a sensor apparatus and method which is self-compensating and thereby capable of giving accurate indication of component concentrations, automatically compensated for variations in the input energy signal or energy level or other variations in the system.

It is another object of this invention to provide an analytical system which enables the practical use of preferred semiconductor laser light sources in fiber-optic sensor devices.

SUMMARY OF THE INVENTION

This invention can be summarized in its most basic aspect as a fiber-optic sensor or analytical apparatus and associated method which utilizes the combination of (a) a solid, semi-solid or liquid sensor body means which is capable of selectively dissolving the compound to be detected and analyzed into the sensor body from the mixture or environment in which the compound is present, and (b) means for causing the compound itself to luminesce while dissolved in the sensor body. This invention thereby enables the device to have dual selectivity, first by selectively dissolving a component into the sensor body and second by selective/specific excitation of the compound to cause it to specifically luminesce in a manner known to be characteristic of that compound. Improved sensitivity is provided by this invention by the direct relationship, i.e., the higher the concentration of the compound, the greater the luminescent signal. The system of this invention eliminates the necessity to use indicators, provides improved selectivity and sensitivity and provides other advantages which will be apparent to one skilled in the art. Having generally summarized this invention, it can be summarized more particularly as follows.

In one aspect, this invention is an analytical apparatus for indicating or measuring the presence or concentration of an analyte component in a fluid mixture containing the analyte comprising:

a source radiant energy means for providing radiant energy suitable for directly exciting the energy level of analyte molecules to an elevated energy state;

selective dissolving means for dissolving the selected analyte molecules from the fluid mixture and excluding any undesired interfering components present in the fluid mixture, for providing a controlled environment in which the analyte molecules are exposed to said source radiant energy to directly excite the analyte molecules to raise the energy level of the analyte molecules to an excited energy state and a controlled environment in which the excited analyte molecules return to a lower energy level and emit radiant energy from the analyte molecules, said selective dissolving means being substantially transparent to the source radiant energy and to the emitted radiant energy;

detection means for measuring the emitted radiant energy and indicating the presence and/or concentration of the analyte present in the fluid mixture;

means for transmitting the source radiant energy from the source radiant energy means to the selective dissolving means; and means for transmitting the emitted radiant energy from the selective dissolving means to said detection means.

In another aspect, this invention is a method for indicating or measuring the presence or concentration of an analyte component in a fluid mixture containing the analyte comprising:

contacting a selective dissolving means with the fluid mixture to dissolve analyte molecules from the fluid mixture, thereby providing a controlled environment in which the analyte molecules are exposed to a source radiant energy to directly excite the analyte molecules to raise the energy level of the analyte molecules to an excited energy state and a controlled environment in which the excited analyte molecules return to a lower energy level and emit radiant energy from the analyte molecules, said selective dissolving means being substantially transparent to the source radiant energy and to the emitted radiant energy;

directing source radiant energy, which is suitable for directly exciting the energy level of analyte molecules to an elevated energy state, into the selective dissolving means to excite the analyte molecules to an excited energy state;

directing the emitted radiant energy from the selective dissolving means to a detection means for measuring the emitted radiant energy;

measuring the emitted radiant energy; and indicating the presence and/or concentration of the analyte in the fluid mixture.

In one particular aspect, the above apparatus and method of this invention are adapted particularly for detecting and analyzing the concentration of gas present in a liquid medium, such as oxygen in blood or other aqueous solution, or a gas present in a gas mixture, such as sulfur dioxide in an effluent gas.

In another particular aspect, the above apparatus and method of this invention are adapted particularly for detecting a liquid component present in a liquid mixture, such as benzene present in a hydrocarbon mixture, or present as a vapor in a gaseous mixture, such as formaldehyde in a workplace environment ambient atmosphere.

Other particular aspects and adaptations of this invention will be apparent to those skilled in the art following the teachings and disclosures of the combinations and their interrelationship constituting the present invention.

BRIEF DESCRIPTION OF THE DRAWINGS

FIG. 1 is a schematic diagram illustrating one embodiment of this invention.

FIG. 2 is a schematic diagram illustrating an embodiment of this invention wherein a single optical fiber is employed.

FIG. 3 is a schematic diagram illustrating an embodiment of this invention for detecting the luminescent signals on the basis of phase shift.

FIG. 4 is a diagram illustrating a time sequence used in the embodiment of FIG. 3.

FIG. 5 is a schematic diagram illustrating an embodiment of this invention which is self-compensating for variations in the input source radiant energy.

FIGS. 6a and 6b are illustrations of one advantageous aspect of this invention of having the analyte dissolved in the sensor body material.

DESCRIPTION OF THE INVENTION

In general, the analytical apparatus of this invention comprises means for transmitting source radiation energy, such as light, through a sensor body containing selective dissolving means having the target analyte component dissolved therein to directly excite that component and cause it to emit luminescent radiation energy, conducting the emitted radiation energy from the sensor body to analytical means where the emitted radiation energy can be analyzed and characterized. The source radiation energy utilized in the devices of this invention can be from any appropriate radiation energy or light source which produces the desired radiation energy or light appropriate to excite the analyte and cause luminescence which can be detected, as described herein. The detector means for receiving the emitted radiation energy or light from the selective dissolving means/ sensor body will contain appropriate means for analyzing and characterizing the emitted light from the analyte component. The analytical means can be adapted to analyze and characterize the emitted radiation or light either in terms of wavelength characteristics or in terms of phase shift compared to the input source radiation energy signal or by other technique. As will be apparent from this disclosure, the analytical means and method of this invention also can be adapted to be self compensating for variations that occur in the apparatus or the operation thereof so that the calibration of the apparatus is easier and more reliable than prior devices.

While this invention is described and illustrated herein primarily in terms of sensing and analyzing for oxygen in aqueous medium, this invention is equally applicable to other gases, vapors or liquids in gaseous or liquid mixtures by applying the principles, apparatus and basic methods of this invention and by adapting appropriate equipment to the particular detection and analysis that is desired.

In part, a basis for this invention is the utilization of the phenomenon that a certain molecule, such as oxygen, can be excited to an energy level above its normal energy state by exposing the molecule to an appropriate source of radiation energy. The source radiation energy imparts certain energy to the molecule changing the electron energy levels to higher levels or higher energy states. When the molecule reverts from its excited energy state to its normal energy state, or to some intermediate level, the molecule will typically emit certain radiation energy. This emitted radiation energy can have different characteristics than the source radiant energy, for example, wavelength, polarization or coherence. Or, this emitted radiation energy may have essentially the same characteristics as the source radiation energy. In the former case, this invention utilizes this phenomenon by detecting the emitted radiation signal based on the different characteristic, such as wavelength, compared to the source radiation by measuring and quantifying the amount of emitted energy and correlating the emitted energy to the concentration of, or quantity of, the analyte molecules present. In the latter case, this invention utilizes a phase shift measurement technique, such as applying the source radiation energy in pulses or sequenced signals, then measuring and quantifying the emitted radiation energy in a phase shift sequence in order to correlate the quantified emitted radiation energy to the concentration or amount of the molecules present. The phase shift can also be employed based on a modulated source energy signal and detecting the emitted energy signal which legs the source energy signal, thus also providing a phase shift basis for detecting the emitted energy.

As an example of a particular embodiment of the present invention, oxygen molecules in a dissolved solution phase can be excited to an elevated energy level using radiation energy from a semiconductor diode type of laser in the wavelength range of about 1270 nm having a power level in the range of 1–7 milliwatts or more. When the oxygen molecules then return to a lower energy level state, or their normal energy level state, they can emit radiation energy in a wavelength range of 1270 to about 1305 nm, all or a portion of which is then detected and analyzed according to the present invention to indicate the presence and/or concentration of the oxygen.

The source radiant energy means useful in connection with the present invention can be any appropriate UV, IR, visible light or other radiation source which has the capability of directly exciting a particular analyte compound molecule to an increased energy level and causing that component to luminesce. The radiation energy source will usually be matched to the analyte compound, which is to be detected and analyzed, so that the light source provides an efficient energy transfer into the analyte component molecule to achieve the higher energy level excited state of the molecule. As described herein, one preferred source radiant energy means is a laser type energy source, and the selective dissolving means and solution phase employed in this invention in particular enables the use of certain preferred narrow emission band lasers when desired for particular applications because of their high intensity and increased efficiency.

The means for transmitting the source radiation energy to the selective dissolving means/sensor body will depend on the radiation energy type, but typically the connection means will be of fiber-optic wave guide means which is adapted for efficient transfer of the source radiation energy. Similarly, selection of the appropriate means for transmitting the emitted radiation energy, as well as the source radiation energy when desired, from the selective dissolving means to the detectors for analysis will be apparent to one skilled in the art.

The selective dissolving means aspect of this invention provides a sensor body which performs a number of important functions in conjunction with and in combination with the other components and elements which make up the analytical apparatus and system according to this invention. The selective dissolving means provides a sensor body which is capable of selectively dissolving or extracting a proportional amount of the desired analyte compound molecules from a gaseous or liquid environment containing the analyte compound when the sensor body is placed in contact with the gaseous or liquid environment or mixture. The selective dissolving means thereby excludes undesired interferring materials or compounds. Interferring compounds or materials are those which would interfere with the dissolving means sensor body being substantially transparent to the source radiation energy and/or the emitted fluorescent radiated energy, which would interfere with the excitation of the analyte compound molecules present therein, which would interfere with, mask or alter in an undesired way the emitted radiation energy from the excited analyte molecules, or which would interfere in some other way. It is to be understood that while the selective dissolving means of this invention is designed and adapted to exclude interferring compounds or materials, there will be situations in which there are no compounds or materials present in the environment being measured which would be interferring or which would interfere in a way which can be tolerated or compensated for in some other way. In such situations there may be nothing significant to exclude or no need to exclude components from entering the selective dissolving means in the sensor body. For example, in the measurement of $SO_2$ in a commercial natural gas stream, there may not be interferring components present which need to be excluded. Nevertheless, a selective dissolving means which is capable of excluding some materials is within the scope of this invention, even if used in a particular application where it is not necessary to exclude materials from the sensor body.

Another important function performed by the selective dissolving means is that once the analyte compound molecules are dissolved into the sensor body, it provides a controlled environment for irradiating those molecules with the source radiation energy in order to excite those molecules to an elevated energy state. Having the analyte compound molecules present in the dissolved or solution phase provides the desired stable and interference free environment for radiating those molecules with the source energy. The selective dissolving means also provides another advantage resulting from having the analyte compound present in the dissolved or solution phase. In some cases, the probability of the source radiant energy causing transition to the excited energy state is significantly increased in the dissolved or solution phase compared to the gas phase. This phenomenon enables the apparatus and method of this inventon to provide desired increases in sensitivity by selecting a particular dissolving means for a particular analyte to provide for optimum efficiency in exciting the analyte molecules for maximum luminescence therefrom, thereby optimizing the sensitivity of the system. In some cases when compounds are excited in the gas phase by radiation energy, they remain in the excited state for a long period of time before they return to the lower energy state and emit the desired light for detection. In some cases that period of time can be several seconds, which generally is impractical for analytical systems desired for many uses. However, in the dissolved or solution phase provided by the selective dissolving means of this invention, the period of time between excitation and emission of the desired light or radiation is very short, such as in the nano-, micro-, or milli-second range, and is usually less than about 1 second, thus providing a practical system for many uses. At the same time, the selective dissolving means sensor body provides an equally controlled environment in which the excited analyte molecules are allowed to return to a lower energy state and thereby emit the luminescent radiant energy which is utilized to provide the analysis according to the present invention. As indicated, this environment precludes interference with either the luminescing or with the luminescent light so that the luminescent light emitted by the excited molecules can be detected, measured and utilized according to this invention.

The selective dissolving means can be any material appropriate for selectively dissolving the desired analyte compound from its environment. Thus, the material can be a solid or semi-solid material, such as a polymer, having the appropriate permeability for the analyte compound to be dissolved therein. In addition, the selective dissolving means can be in a sensor body comprising a liquid and a semi-permeable membrane which interfaces between the liquid and the environment containing the analyte compound. The semi-permeable membrane serves to selectively pass the analyte compound into the liquid while excluding undesired or interfering compounds or materials from being dissolved in the liquid in the sensor body. Such a semi-permeable membrane can be used not only with a liquid dissolving means, but with any dissolving means material. Also, such a membrane enables the use of materials as dissolving means which may not per se be sufficiently selective, but in combination with an appropriate semi-permeable membrane will provide the desired selectivity and the desired dissolving means functions, as described herein. In addition, such a membrane itself need not be transparent to the radiant energies involved, but needs only to have the appropriate permeability. In fact, it may be preferable to use a membrane which is or can be made reflective on the inside surface to function or aid in the sensor body serving as a light guide over the length of the sensor body to retain, collect and direct the source and/or emitted radiant energies as described herein. Instead of being reflective, the membrane may serve the same function by having an appropriate refractive index lower than the dissolving material in the sensor body, thereby causing the sensor body to have the desired light guide properties. Materials which can be used for semi-permeable membranes include such polymers as polytetrafluoroethylene, polyethylene, polydimethlysiloxane, and the like. Other forms of the selective dissolving means which meet the above criteria for functioning in the analytical apparatus of the present invention can be selected by one skilled in the art and depending on the particular environment and analyte compound involved.

Examples of materials suitable for use as the selective dissolving means according to this invention include certain polydimethylsiloxane materials which are known to be useful in aqueous solutions and are effective in allowing $CO_2$, oxygen, benzene, formaldehyde and other gases, vapors or liquids to permeate into the polydimethylsiloxane material. The polydimethylsiloxane materials are also substantially transparent to most energy radiation wavelengths of interest in this invention. Other polymeric materials suitable for use in this invention include polybutadiene, styrene-butadiene rubber, poly(2,6-diphenyl-1, 4-phenylene oxide), polyethylene, poly(4-methyl-pentene-1), polytetrafluoroethylene, poly(chlorotrifluoro)ethylene, polystyrene, polychloroprene, butadiene-acrylonitrile rubber, polymethylmethacrylate, polyurethane, polycarbonate, silicone and the like.

As used herein luminescence is used to include both flourescence and phosphorescence.

As used herein the term "dissolving" includes not only its convention meaning of a gas or other material dissolved in a liquid but also includes within its means the physical phenomenon wherein a gas, liquid or other material is absorbed into or permeates a solid or semi-solid material whereby it is free to diffuse through and migrate in solid or semi-solid material in response to concentration gradiants. That is, so long as the behavior is similar to the material in a liquid solution, it is included in the scope of this invention even though the "solution" or "dissolving" is present in a solid or semi-solid material.

As used herein the term "molecules" includes not only actual molecules but the atomic form of the elements as well. The atomic forms are included in the scope of this invention to the extent that it can be excited to an elevated energy state by source radiation and emit luminescent radiation when it returns to a lower energy state. The same is true for compounds or complexes which may not fit the conventional definition of molecules, but as long as they perform as indicated in the present invention, they are considered to be "molecules" within the meaning of the term as used herein.

As will be recognized by one skilled in the art, any combination of the present invention provides various advantages in the selectivity and sensitivity of the analytical apparatus provided by this invention. The sensitivity provided by this invention as discussed herein, is primarily due to the direct measurement of luminescent light which is emitted directly by and from the analyte compound of interest. The selectivity of the analytical apparatus of the present invention is provided by the unique combination of a number of aspects. First is the selectivity provided by the selective dissolving means which can be designed to dissolve the analyte of interest and exclude other materials of which are not of interest. This is done, as indicated above, by selecting a solid or semi-solid material for use in the sensor body or can be accomplished by using a liquid selective dissolving means in combination with a semi-permeable membrane to interface with the environment being analyzed. Of course, combinations thereof can be used to achieve the dissolving activity desired. For example, a selective solid or semi-solid material can be used in combination with a semi-permeable membrane to provide additional activity for the particular analyte compound to enter the sensor body and be subject to analysis according to this invention. In addition, added selectivity is provided by using this selective dissolving means in combination with a particular source radiant energy and further in combination with detection means which receives and analyzes only the emitted luminescent energy of interest from the analyte compound of interest while excluding other radiant energy which may be present. Since some analyte compounds are only excited to elevated energy levels source radiant energy of a specific wavelength, a light source providing only that particular wavelength, whether it is achieved by the source itself or by filters, can be used to specifically excite the analyte compound of interest and avoid exciting other materials or compounds causing interferring fluorescence. In addition, even if a broad spectrum source radiant energy is used and a number of compounds or materials may luminesce, the luminescent energy of the analyte compound of interest may still be singled out by identification of its unique wavelength or luminescence lifetime thereby providing highly selective analytical results, even when the source radiant energy or the selective dissolving means are not themselves particularly selective. Obviously, when the combination of a highly selective dissolving means, a highly selective source radiant energy and a highly selective emitted luminescent radiant energy detection are all used in combination, the selectivity of the analytical apparatus of this invention can be maximized. As is also apparent in such an optimum combination, the sensitivity can also be optimized.

The application of this invention is discussed primarily herein in terms of oxygen. As will be recognized by one skilled in the art, this invention is applicable to any analyte compound or material which can be excited to an elevated energy state by source radiant energy and which will emit radiant energy when it returns to a lower or its normal energy state. The sensitivity and utility will obviously depend on the particular analyte compound properties and especially on the characteristics of the luminescent radiant energy which the material or compound will emit. In addition to oxygen, this invention can be used for benzene which can be excited by light in a wavelength range of about 250 to about 260 nm and which emits luminescent energy in the range of about 270–300 nm, formaldehyde can be excited at a wavelength range of about 325 to about 350 nm and will luminesce at about 360–440 nm, sulfur dioxide can be excited at about 210 nm and will luminesce at about 240–420 nm, $N_2O$ can be excited at wavelength of about 4.5 micron and will luminesce at about 4.5 micron, $NO_2$ can be excited at about 405 to about 440nm and will luminesce at about 560–655 nm. Other materials such as carbon dioxide may be more difficult to detect because they emit the fluorescent energy at very low wavelengths in the infrared range, and a portion is dissipated as heat. However, with the proper sensors and detectors, the apparatus of this invention can be adapted to and be useful to analyzing those materials as well.

It is a straightforward matter to adapt this invention to other analytes as well. If the necessary excitation/luminescence information is not available as reference information for a particular analyte of interest, a pure test sample of the analyte can be subjected to radiation of varied wavelengths and intensities to determine if it will luminesce sufficiently under practical conditions to be useful in this invention. If so, then the source radiant energy means and the emitted radiant energy detection means can be selected accordingly, along with other appropriate components used in the apparatus and method of this invention. Similarly, once a particular analyte is selected, such as by the above procedure, then the materials can be selected for the selective dissolving means and for other components of the sensor body based on the properites of the analyte and the environment in which it will be detected and analyzed according to this invention.

The emitted radiation energy detection means can be any means which is appropriate for detecting and measuring the radiation energy emitted by the analyte molecules when they return from the excited energy level state to a lower or normal energy level state. Among the considerations to be taken into account in selecting the detection and analytical means are whether the detection is to be a wavelength detection at a different range for the emitted signal than for the originating signal or whether the detection is to detect a phase shift in the emitted radiation energy versus the source radiation energy. In general, photodetectors are used in conjunction with the appropriate equipment, such as lock-in amplifiers, box car averagers, etc.

An embodiment of this invention, illustrated in FIG. 1, is a sensor for the measurement of the concentration of oxygen in an aqueous medium, such as blood or water. In the sensor system in FIG. 1, laser diode 1 (Toshiba Model TOLD300A) emits source light of a wavelength equal to 1270 nm into the first end optical fiber 3 (Ensign-Bickford HCP-B08-T) with a core diameter of 120 µm. The source light is coupled into the fiber by what is commonly known as a "pig-tail" connection. Attached to the second end of optical fiber 3 is selective dissolving means 4, which is a linear filament of polydimethylsiloxane (Petrarch Systems type PS273). This selective dissolving means filament 4 is approximately the same diameter as the optical fiber 3 and its first end is bonded to the second end of optical fiber 3.

When selective dissolving means 4 is placed in the aqueous medium containing oxygen, oxygen present in the aqueous medium will permeate the polydimethylsiloxane filament and will become dissolved in the polydimethylsiloxane. A portion of the oxygen dissolved in the polydimethylsiloxane will absorb a portion of the 1270 nm source light which is passing through the polydimethylsiloxane from diode 1 and optical fiber 3, thereby forming oxygen molecules which are in an excited energy state. A portion of the excited oxygen molecules which absorbs the 1270 nm source light will luminesce within 1 millisecond. A portion of the longer wavelength emitted light Will be coupled into optical fiber 5, the first end of which is bonded to the second end of the polydimethylsiloxane filament.

The second end of fiber 5 is placed at the focus of lens 6, so that any light leaving the fiber will be collimated after passing through lens 6. The collimated light will strike interference filter 8 (Omega Optical type BP, or preferably, type GF), which selectively passes the emitted luminescent light and blocks the remaining 1270 nm source light. The emitted luminescent light is then focused onto photodetector 10 (Germanium Power Devices Corporation type GM-3), by lens 9. The intensity of the emitted luminescent light, which is proportional to the concentration of oxygen in the aqueous medium environment surrounding the filament, is converted into an electrical current by photodetector 10, and fed into lock-in amplifier 13 (Stanford Research Model SR510). Lock-in amplifier 13 is referenced to the laser driver which modulates the laser diode 1. The output signal from the lock-in signal is then input to a suitable signal processing unit, such as microcomputer 14. The oxygen partial pressure in the aqueous medium environment surrounding the selective dissolving means 4 is calculated according to the equation:

$$pO2 = K \; S$$

where the term K is a constant and S is the signal from the lock-in amplifier. The resulting value for the partial pressure, i.e., concentration, of oxygen, is displayed in display 15.

FIG. 2 illustrates an embodiment of this invention where the sensor system uses a single optical fiber. This configuration is more compact than that illustrated in FIG. 1 and may be advantageous in certain applications, such as in catheter devices for in vivo uses. Source light from laser diode 201 (Toshiba Model TOLD300A emitting at 1270 nm or Sharp Model LT031MD0 emitting at 760 nm) is collimated by lens 202 and passes through beamsplitter 203. In certain applications, it will be advantageous for beamsplitter 203 to be coated to render it a dichroic beamsplitter. The source light is focused into optical fiber 205 by lens 204 and transmitted by optical fiber 205 to sensor tip 206. Sensor tip 206 is a selective dissolving means which can be constructed either of suitable polymer, such as Petrarch Systems type PS273 polydimethylsiloxane, or can be a capillary tube sealed to optical fiber 205 at one end, sealed with a suitable gas permeable membrane at the other end, and filled with a suitable liquid which is substantially transparent to both the exciting source light and the emitted luminescent light and which is a good solvent for oxygen. In the catheter type devices, the selective dissolving means can be contained in or otherwise carried by a catheter means adapted for in vivo blood contact, thereby providing a device for in vivo blood gas analysis. In some applications, the sides and end of the sensor tip 206 may be covered with a suitable light reflective material, or a material with a refractive index such as to promote total internal reflection to maximize the light directed into fiber 205 and to detector 209. As mentioned above, the sensor body 206 can include a dissolving material and a semipermeable membrane which is reflective on the inside surface to provide this desired effect.

Oxygen in the environment surrounding the sensor tip will permeate the sensor tip 206 and become dissolved in the polymer or liquid present in sensor tip 206. As in FIG. 1 above, the oxygen will absorb a portion of the exciting source light and become excited oxygen molecules. A portion of the excited oxygen molecules which absorb the exciting source light will luminesce. The intensity of this emitted luminescence will be porportional to the concentration of oxygen in the environment surrounding selective dissolving means sensor tip 206.

The portion of the emitted lumuniscent light, together with a portion of the exciting source light, which is back-scattered or reflected, is transmitted from sensor tip 206 into optical fiber 205 and carried to lens 204. Lens 204 collimates this light and a portion of it is directed by beamsplitter 203 onto optical interference filter 207 (Omega Optical Type GF), which selectively blocks the exciting source light and transmits the emitted luminiscent light. The emitted luminescent light is focused by lens 208 onto photodetector 209 (Germanium Power Devices Corporation Type GM-2). The resulting electrical signal is fed to lock-in amplifier 211 (Stanford Research Systems Model SR510), which is connected to a modulator (Wavetek Model 184 Sweep Generator) and a microprocessor based signal processor 212 and display 213, where the partial pressure or concentration of oxygen is displayed as in FIG. 1.

Another embodiment of this invention, illustrated in FIG. 3, comprises a sensor and method for the measurement of the concentration of oxygen in a fluid, such as blood or water. The sensor system in FIG. 3 shows laser diode 301 (Toshiba Model TOLD300A) emitting source light of a wavelength equal to 1270 nm into the first end of optical fiber 302 (Ensign-Bickford HCP-B08-T) with a core diameter of 120 μm. The source light is coupled into the fiber 302 by what is commonly known as a "pig-tail" connection. Attached to the second end of fiber 302 is selective dissolving means sensor body 303, which comprises a linear filament of polydimethylsiloxane (Petrarch Systems type PS273). This sensor filament 303 is approximately the same diameter as the optical fiber 302 and the first end of sensor filament 303 is bonded to the second end of optical fiber 302.

Oxygen dissolved in a fluid surrounding the sensor filament 303 will permeate the sensor filament and is dissolved in the polydimethylsiloxane. The selective dissolving means sensor body 303 excludes components of the fluid mixture which would interfere with the source light, the emitted light or with exciting the oxygen molecules to a higher energy level. A portion of the oxygen dissolved in the polydimethylsiloxane sensor body 303 will absorb a portion of the 1270 nm source light which is passing through sensor filament 303. A portion of the excited oxygen which has absorbed the 1270 nm light will emit luminescence and a portion of the emitted luminiscent light will be coupled into optical fiber 304, the first end of which is bonded to the second end of sensor filament 303. The second end of fiber 304 is placed adjacent to photodetector 305 (Germanium Power Devices Corporation type GM-3) so that any light leaving the fiber will impinge on photodetector 305.

As illustrated in the timing diagram in FIG. 4, at time $t_o$ laser diode 301 is turned on for a fixed period of time by laser diode driver 306. During the time that the laser diode is on, excited state oxygen will be generated as the exciting source light passing into sensor tip 303 is absorbed by oxygen contained within the sensor tip 303. At time $t_1$, the laser diode 301 is turned off. During the time between $t_1$ and $t_2$, the dissolved oxygen present in sensor tip 303 continues to luminesce as the excited state oxygen decays back to the original ground energy level state. During this time period between $t_1$ and $t_2$, the intensity of the emitted luminescent light, which is proportional to the concentration of oxygen in the environment surrounding the sensor filament 303, is converted into an electrical current by photodetector 305, which is fed into amplifier 307. The output signal from amplifier 307 is then input to a suitable signal processing unit, such as microcomputer 308, and integrated. At time $t_2$, the signal integration is stopped and the laser diode 301 is again turned on for time interval $t_2$ to $t_3$ and the cycle repeated. The partial pressure of oxygen in the environment surrounding the sensor is calculated from the integrated signal, or from the average integrated signal, from a multitude of cycles, and the result is shown on display 309.

FIG. 5 illustrates another embodiment of this invention which is self-compensating, i.e., will automatically compensate for variations in the input source energy leval. The optical output of a laser diode 501 is that of FIG. 1 and emits light of a wavelength which can be absorbed by oxygen, is coupled into the first end of optical fiber 503 (Ensign-Bickford HCP-BO8-T) by lens 502. Attached to the second end of fiber 503 is selective dissolving means sensor body 504, which is a linear filament of polydimethylsiloxane (Petrarch Systems type PS273). This filament 504 is approximately the same diameter as optical fiber 503 and the first end of filament 504 is bonded to the second end of optical fiber 503.

Oxygen present in a fluid surrounding polydimethylsiloxane sensor body 504 will permeate and become dissolved in the polydimethylsiloxane. A portion of the oxygen dissolved therein will absorb a portion of the source light from laser diode 501, which light is passing through sensor body 504, thereby forming oxygen molecules that are in an excited energy state. A portion of the emitted luminiscent light, together with the unabsorbed source light from the laser diode 501 will be coupled into optical fiber 505, the first end of which is bonded to the second end of sensor body 504. The second end of fiber is placed at the focus of lens 506 so that the light leaving fiber 505 will be collimated after passing through lens 506. The collimated light is directed to beamsplitter 507 and will be split into two beams, one of which will be focused by lens 511 onto photodetector 512, and the other of which will be directed onto optical interference filter 508. Interference filter 508 blocks the light from laser diode 501, but passes the emitted luminescent light from the excited state oxygen in the sensor body 504. Since the absorptivity of oxygen is low ($1.2 \times 10^{-5}$ cm$^{-1}$ atm$^{-1}$ for the 760 nm absorption and $8.5 \times 10^{-5}$ cm$^{-1}$ atm$^{-1}$ for the 1270 nm absorption), the amount of light received by photodetector 512 will essentially be independent of oxygen present in sensor body 504, but will be directly proportional to the intensity of the source light from laser diode 501. The amount of emitted luminescent light received by photodetector 510 will be proportional to the concentration of oxygen in the sensor body 504 in accordance with the following:

$$L_1 = I_o \phi_f \phi_e \epsilon 1 C \tag{1}$$

where $L_1$ is the amount of emitted luminescent light received by photodetector 510, $I_o$ is the intensity of the source light from laser diode 501 which is transmitted to the sensor body 504, $\phi_f$ is the luminescence quantum yield for oxygen, $\phi_e$ is a term related to the optical efficiency of the system, $\epsilon$ is the extinction coefficient of oxygen, 1 is the effective optical pathlength of the sensor body 504 and C is the concentration of oxygen dissolved in sensor body 504. The partial pressure of oxygen in the environment surrounding the sensor 504, pO2, can thus be expressed as:

$$pO2 = S_1/(K\ S_2) \tag{2}$$

where $S_1$ is the electrical signal from amplifier 513 produced from the signal from photodetector 510, $S_2$ is the electrical signal from amplifier 513 produced from the signal from photodetector 512, and K is a constant which incorporates a number of factors, including the constants $\phi_f$, $\phi_e$, $\epsilon$, and 1, as well as the coefficients for the response of the detectors, the partition coefficient for the partitioning of oxygen between the polydimethylsiloxane of the sensor body and the surrounding environment. Depending on the circumstances, it may be necessary to add a second constant, $K_2$, to account for various offsets of the system. The oxygen partial pressure can be calculated by signal processor 514 according to the equation:

$$pO2 = S_1/(K_1 S_2) + K_2 \tag{3}$$

where $K_1$ and $K_2$ can be determined from a calibration curve or, in certain cases, from the known valves of the relevant constants for the system in question. The oxygen partial pressure or oxygen concentration is displayed on indicator means 515.

As previously indicated herein, prior art sensors which work on the basis of fluorescence quenching contain an indicator which fluoresces in the absence of oxygen. As the oxygen concentration increases, the intensity of fluorescence from the indicator in such an oxygen sensor decreases. Thus, such sensors have the disadvantage of giving an inversely proportional indication, which causes difficulty in obtaining the desired sensitivity over the desired range of operation of the sensor.

One of the advantages of the sensor of the present invention resides in the fact that the intensity of the emitted luminescent radiation energy increases as the analyte compound concentration increases. This sensor responds in a positive sense, and is very sensitive since it employs a zero background technique, i.e., in the absence of analyte there will be no signal. In general, the luminescence from an analyte species such as oxygen is related to its concentration according to the equation:

$$L = I_o \phi_F f(\Theta) g(x) (1 - e^{-\epsilon l C}) \tag{4}$$

where L is the luminescence intensity, $I_o$ is the intensity of the source exciting light, $\phi_F$ is the luminescence quantum yield, $f(\Theta)$ is a function which accounts for the optical efficiency of the apparatus used in the experiment, $g(x)$ is a function which describes the wavelength sensitivity of the optical system and detection electronics, $\epsilon$ is the extinction coefficient for the absorbing compound, 1 is the effective pathlength for absorption, and C is the concentration of the compound. (Willard, Merritt, Dean and Settle, *Instrumental Methods of Analysis*, Sixth Edition, Wadsworth Publishing, Belmont, California, 1981.) In cases where less than 2% of the total source radiant energy, or excitation light, is absorbed by the analyte in elevating its energy state so it will then emit luminescent radiant energy, as in the case with many analytes, particularly oxygen, then this expression simplifies to:

$$L = I_o \phi_F f(\Theta) g(x) \epsilon 1 C \tag{5}$$

and the observed emitted luminescence intensity will be directly proportional to the concentration, C, of the analyte compound being measured. This invention thus enables simple and direct calculation of the analyte concentration.

As previously indicated herein, another advantage provided by this invention is that it enables the use of solid state laser diodes as the source radiant energy means. Laser diodes are attractive sources for use with fiber-optic sensors because they are efficient and provide very high intensities. Since the intensity of the fluorescent light, L, emitted from the analyte molecules is directly proportional to the intensity of the source radiant energy, or exciting light, $I_o$, as shown by equation (5) above, using a high intensity source light $I_o$ is advantageous.

In order to excite oxygen, or other analyte molecules, the absorption spectrum of the particular molecule must overlap with the emission spectrum of the source exciting light being used. Laser diodes produce a high intensity emission, but the spectrum of the emission is usually a very narrow line with a center wavelength that can vary with changes in temperature, power or other conditions. For many analytes, such as gases, the absorption spectrum of the analyte in the gas phase consists of a series of very narrow absorption lines. This can be seen in the upper graph of FIG. 6a, which is a schematic representation of the gas phase absorbance spectrum for oxygen. The bottom graph in FIG. 6a illustrates the output of a laser diode. If the laser diode source light is at a wavelength between the absorption bands of the oxygen, the oxygen will not be excited to an elevated energy state and will not luminesce. Since it can be difficult to control the output of a laser diode so that the narrow emission line of the laser diode continuously overlaps one of the narrow absorption lines of the gas phase oxygen for an extended period of time, it is impractical to use a laser diode as the source light.

However, when an analyte gas, such as oxygen, is dissolved in a liquid, solid or polymeric material, as utilized by the selective dissolving means sensor body of this invention, the resulting solution shows an absorption spectrum in which the narrow absorption lines broaden and typically overlap. For example, FIG. 6b illustrates in the upper graph is a schematic representation of the absorbance spectrum for oxygen dissolved in a solution phase. Since the absorption spectrum under these solution conditions tends to be broad and continuous, it is far easier to maintain overlap between the laser light emission illustrated by the lower graph of FIG. 6b, and the analyte absorption spectrum. Thus, the use of a selective dissolving means in the sensor body to form a solution of the analyte molecules offers a distinct advantage over the use of a gas-filled sensor body chamber, because laser diodes can be easily used as excitation sources.

Another advantage that is provided by the selective dissolving means of this invention as used in the apparatus of this invention is that it allows for the excitation of large number of analyte molecules, i.e., a relatively large volume of dissolving material containing the analyte compound, and it allows for the efficient collection of the resulting luminescent light without the use of auxiliary optical components, such as lens, to achieve the desired sensitivity of the measurement. By correctly selecting the material used in the selective dissolving means, and, in some circumstances selecting a particular shape of the sensor body, the selective dissolving means can guide and direct the exciting radiant energy as well as collect, guide, and direct the emitted radiant energy in a way that the sensitivity of the analytical apparatus is greatly enhanced. For instance, by choosing the index of refraction of the selective dissolving means so that it is greater than the index of refraction of the surrounding environment or by coating it with a suitable material of lower refractive index than the refractive index of the dissolving material, the selective dissolving means can act as a waveguide for both the exciting radiant energy and the emitted radiant energy. An example would be to use a filament of polydimethylsiloxane ($n_D$=1.43) as the selective dissolving means for the measurement of oxygen in breathing gas ($n_D \approx 1.00$).

Similarly, having the selective dissolving means/sensor body function as a light guide, serves to maintain the intensity of the source radiant energy throughout the selective dissolving means, particularly where the dissolving means is a long length of material. This not only prevents divergence and loss of the source radiation energy in the sensor body, it also provides maximum collection and transmission of the emitted luminescent energy from the analyte compound to the detection means.

What is claimed is:

1. Analytical apparatus for indicating the presence of an analyte component in a fluid mixture containing the analyte comprising:

(i) a source radiant energy means adapted for providing selected wave length radiant energy suitable for directly exciting oxygen analyte molecules to an elevated energy state;

(ii) a polymeric selective dissolving means, said dissolving means constituting a waveguide;

(iii) detection means for measuring the radiant energy emitted from the analyte molecules and indicating the presence of the analyte present in the fluid mixture;

(iv) means for transmitting the source radiant energy from the source radiant energy means to the analyte molecules in the selective dissolving means; and (v) means for transmitting the emitted radiant energy from the selective dissolving means to said detection means;

wherein said selective dissolving means is adapted for contacting the fluid mixture, for dissolving the selected analyte molecules from the fluid mixture, for providing the analyte molecules in the dissolved or solution phase in the selective dissolving means, for excluding undesired interfering components present in the fluid mixture, and for providing a controlled environment in which the analyte molecules are exposed to said source radiant energy to directly excite the dissolved or solution phase analyte molecules and raise the energy level of the analyte molecules to an excited energy state and a controlled environment in which the excited analyte molecules return to a lower energy level and emit radiant energy from the analyte molecules, and wherein said selective dissolving means is substantially transparent to the source radiant energy and to the emitted radiant energy, and is of a shape and material selected to be effective for collecting, guiding and directing emitted radiant energy.

2. An apparatus according to claim 1, wherein the detection means comprises means for indicating the concentration of the analyte present in the fluid mixture.

3. An apparatus according to claim 1, wherein the selective dissolving means comprises material for dissolving the analyte and a semipermeable membrane as interface means between said material and the fluid mixture.

4. An apparatus according to claim 1, wherein the selective dissolving means comprises means for preventing loss of emitted radiant energy and means for directing the emitted radiant energy to the means for transmitting the emitted radiant energy to the detection means.

5. An apparatus according to claim 1, wherein the selective dissolving means comprises means for preventing loss of emitted radiant energy and means for directing the emitted radiant energy to the means for transmitting the emitted radiant energy to the detection means.

6. An apparatus according to claim 1, comprising means for compensating the indication of concentration of analyte for variations occurring in the apparatus or during the operation thereof.

7. An apparatus according to claim 1, wherein the detection means comprises means for measuring the emitted radiant energy based on a phase shift of the emitted radiant energy compared to the source radiant energy.

8. An apparatus according to claim 1, comprising catheter means adapted for in vivo blood gas analysis.

9. An apparatus according to claim 1, wherein the detection means comprises means for measuring the emitted radiant energy based on a characteristic of the emitted radiant energy which is different from the characteristics of the source radiant energy.

10. An apparatus according to claim 9, wherein the characteristic is wavelength.

11. An apparatus according to claim 1, wherein said selective dissolving means is of a shape and material selected to be effective for at least one of guiding and directing the exciting radiant energy.

12. An apparatus according to claim 11, wherein the detection means comprises means for indicating the concentration of the analyte present in the fluid mixture.

13. An apparatus according to claim 11, wherein the selective dissolving means comprises material for dissolving the analyte and a semipermeable membrane as interface means between said material and the fluid mixture.

14. An apparatus according to claim 11, comprising means for compensating the indication of concentration of analyte for variations occurring in the apparatus or during the operation thereof.

15. An apparatus according to claim 11, wherein the detection means comprises means for measuring the emitted radiant energy based on a phase shift of the emitted radiant energy compared to the source radiant energy.

16. An apparatus according to claim 11, wherein the detection means comprises means for measuring the emitted radiant energy based on a characteristic of the emitted radiant energy which is different from the characteristics of the source radiant energy.

17. An apparatus according to claim 16, wherein the characteristic is wavelength.

18. Analytical apparatus for indicating the presence of an analyte component in a fluid mixture containing the analyte comprising:
  (i) a source radiant energy means adapted for providing selected wave length radiant energy suitable for directly exciting oxygen analyte molecules to an elevated energy state;
  (ii) a polymeric selective dissolving means said dissolving means constituting a waveguide;
  (iii) detection means for measuring the radiant energy emitted from the analyte molecules and indicating the presence of the analyte present in the fluid mixture;
  (iv) means for transmitting the source radiant energy from the source radiant energy means to the analyte molecules in the selective dissolving means; and
  (v) means for transmitting the emitted radiant energy from the selective dissolving means to said detection means;
  wherein said selective dissolving means is adapted for contacting the fluid mixture, for dissolving the selected analyte molecules from the fluid mixture, for providing the analyte molecules in the dissolved or solution phase in the selective dissolving means, for excluding undesired interfering components present in the fluid mixture, and for providing a controlled environment in which the analyte molecules are exposed to said source radiant energy to directly excite the dissolved or solution phase analyte molecules and raise the energy level of the analyte molecules to an excited energy state and a controlled environment in which the excited analyte molecules return to a lower energy level and emit radiant energy from the analyte molecules, and wherein said selective dissolving means is substantially transparent to the source radiant energy and to the emitted radiant energy, and is of a shape and material selected to be effective for at least one of guiding and directing exciting radiant energy.

19. An apparatus according to claim 18 comprising catheter means adapted for in vivo blood gas analysis.

20. A method for indicating the presence of an oxygen analyte component in a fluid mixture containing the analyte comprising:
  (a) selecting and contacting a polymeric selective dissolving means said dissolving means, constituting a waveguide, with the fluid mixture to dissolve the analyte molecules from the fluid mixture, to provide the analyte molecules in the dissolved or solution phase in the selective dissolving means, and to provide a controlled environment in which the analyte molecules are exposed to a source radiant energy to directly excite the analyte molecules and raise the energy level of the analyte molecules to an excited energy state and a controlled environment in which the excited analyte molecules return to a lower energy level and emit radiant energy from the analyte molecules, wherein said selective dissolving means is selected such that it is substantially transparent to the source
  (b) directing source radiant energy, which is suitable for directly exciting the analyte molecules to an elevated energy state, into the selective dissolving means to directly excite the dissolved or solution phase analyte molecules to an excited energy state;
  (c) directing the radiant energy emitted from the analyte molecules from the selective dissolving means to a detection means for measuring the emitted radiant energy;
  (d) measuring the emitted radiant energy; and
  (e) indicating the presence of the analyte.

21. A method according to claim 20 comprising employing the selective dissolving means in the form of a catheter and measuring a blood gas in vivo.

* * * * *